(12) United States Patent
Caparso et al.

(10) Patent No.: US 7,617,003 B2
(45) Date of Patent: Nov. 10, 2009

(54) SYSTEM FOR SELECTIVE ACTIVATION OF A NERVE TRUNK USING A TRANSVASCULAR RESHAPING LEAD

(75) Inventors: Anthony Caparso, St. Louis Park, MN (US); Julia Moffitt, North Liberty, IA (US); Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 705 days.

(21) Appl. No.: 11/130,022

(22) Filed: May 16, 2005

(65) Prior Publication Data

US 2006/0259107 A1    Nov. 16, 2006

(51) Int. Cl.
*A61N 1/05* (2006.01)
(52) U.S. Cl. .................. 607/116; 607/117
(58) Field of Classification Search .......... 607/115, 607/116, 117, 119, 122, 126
See application file for complete search history.

(56) References Cited

U.S. PATENT DOCUMENTS

| | | | |
|---|---|---|---|
| 4,217,910 A | 8/1980 | Khalil | |
| 5,324,316 A | 6/1994 | Schulman et al. | |
| 5,354,318 A | 10/1994 | Taepke | |
| 5,501,703 A * | 3/1996 | Holsheimer et al. | 607/46 |
| 5,522,854 A | 6/1996 | Ideker et al. | |
| 5,531,779 A * | 7/1996 | Dahl et al. | 607/119 |
| 5,540,730 A | 7/1996 | Terry, Jr. et al. | |
| 6,006,134 A | 12/1999 | Hill et al. | |
| 6,141,588 A | 10/2000 | Cox et al. | |
| 6,164,284 A | 12/2000 | Schulman et al. | |
| 6,205,361 B1 * | 3/2001 | Kuzma et al. | 607/116 |
| 6,240,316 B1 | 5/2001 | Richmond et al. | |
| 6,292,695 B1 | 9/2001 | Webster, Jr. et al. | |
| 6,445,953 B1 | 9/2002 | Bulkes et al. | |
| 6,456,866 B1 | 9/2002 | Tyler et al. | |
| 6,522,926 B1 | 2/2003 | Kieval et al. | |
| 6,564,096 B2 | 5/2003 | Mest | |
| 6,584,362 B1 | 6/2003 | Scheiner et al. | |

(Continued)

FOREIGN PATENT DOCUMENTS

EP    1304135 A2    4/2003

(Continued)

OTHER PUBLICATIONS

"U.S. Appl. No. 11/103,245, Non-Final Office Action mailed Jan. 11, 2008", 9 pgs.

(Continued)

*Primary Examiner*—Carl H. Layno
*Assistant Examiner*—Jon-Eric C. Morales
(74) *Attorney, Agent, or Firm*—Schwegman, Lundberg & Woessner, P.A.

(57) ABSTRACT

A system for selective activation of a nerve trunk using a transvascular reshaping lead is provided. One aspect of this disclosure relates to a system for spreading nerve bundles in a nerve trunk. The system includes a lead adapted to be chronically implanted in a blood vessel proximate a nerve trunk, and having an expandable portion adapted to be expanded to reshape the blood vessel to an elongated shape and to reshape the nerve trunk into an elongated shape to spread nerve bundles of the nerve trunk. The system also includes a plurality of electrodes and an implantable device coupled to the lead, where an electrical signal is delivered from the implanted medical device to one of the plurality of electrodes to transvascularly deliver neural stimulation from the electrode to at least one of the nerve bundles of the nerve trunk. Other aspects and embodiments are provided herein.

42 Claims, 8 Drawing Sheets

U.S. PATENT DOCUMENTS

| | | | |
|---|---|---|---|
| 6,656,960 B2 | 12/2003 | Puskas | |
| 6,778,854 B2 | 8/2004 | Puskas | |
| 6,804,561 B2 | 10/2004 | Stover | |
| RE38,705 E | 2/2005 | Hill et al. | |
| 6,934,583 B2 | 8/2005 | Weinberg et al. | |
| 2002/0026221 A1 | 2/2002 | Hill et al. | |
| 2002/0042637 A1 | 4/2002 | Stover | |
| 2002/0107557 A1 | 8/2002 | Edell et al. | |
| 2002/0161410 A1 | 10/2002 | Kramer et al. | |
| 2002/0183237 A1 | 12/2002 | Puskas | |
| 2002/0198570 A1 | 12/2002 | Puskas | |
| 2002/0198571 A1 | 12/2002 | Puskas | |
| 2003/0074039 A1 | 4/2003 | Puskas | |
| 2003/0114905 A1 | 6/2003 | Kuzma | |
| 2003/0195578 A1 | 10/2003 | Perron et al. | |
| 2003/0199958 A1 | 10/2003 | Zhang et al. | |
| 2004/0030362 A1 | 2/2004 | Hill et al. | |
| 2004/0059383 A1 | 3/2004 | Puskas | |
| 2004/0186531 A1 | 9/2004 | Jahns et al. | |
| 2005/0065553 A1 | 3/2005 | Ben Ezra et al. | |
| 2005/0085864 A1 | 4/2005 | Schulman et al. | |
| 2005/0143412 A1 | 6/2005 | Puskas | |
| 2005/0149156 A1* | 7/2005 | Libbus et al. | 607/119 |
| 2005/0187584 A1 | 8/2005 | Denker et al. | |
| 2005/0197675 A1 | 9/2005 | David et al. | |
| 2006/0229677 A1 | 10/2006 | Moffitt et al. | |

FOREIGN PATENT DOCUMENTS

| | | |
|---|---|---|
| WO | WO-94/07564 A2 | 4/1994 |
| WO | WO-99/65561 A1 | 12/1999 |
| WO | WO-2006/110338 A1 | 10/2006 |

OTHER PUBLICATIONS

"U.S. Appl. No. 11/103,245, Response filed Oct. 17, 2007 to Restriction Requirement mailed Sep. 18, 2007", 7 pgs.

"U.S. Appl. No. 11/103,245, Restriction Requirement mailed Sep. 18, 2007", 6 pgs.

Dunlap, M. E., et al., "Mechanisms of Altered Vagal Control in Heart Failure: Influence of Muscarinic Receptors and Acetylcholinesterase Activity", *Am J Physiol Heart Circ Physiol.*, 285(4), (2003), H1632-H1640.

Grassi, G., et al., "Sympathetic Response to Ventricular Extrasystolic Beats in Hypertension and Heart Failure", *Hypertension*, 39(4), (Apr. 2002), 886-91.

Leventhal, D K., et al., "Subfascicle Stimulation Selectivity with the Flat Interface Nerve Electrode", *Annals of Biomedical Engineering*, 31(6), (2003), 643-652.

Li, M., "Vagal Nerve Stimulation Markedly Improves Long-Term Survival After Chronic Heart Failure in Rats", *Circulation*, 109(1), (2004), 1-5.

Nolan, J., et al., "Prospective Study of Heart Rate Variability and Mortality in Chronic Heart Failure: Results of the United Kingdom Heart Failure Evaluation and Assessment of Risk Trial (UK-Heart).", *Circulation*, 98(15), (1998), 1510-1516.

Schauerte, P., "Catheter Stimulation of Cardiac Parasympathetic Nerves in Humans: A Novel Approach to the Cardiac Autonomic Nervous System", *Circulation*, 104(20), (2001), 2430-2435.

Schauerte, P. N., et al., "Transvenous Parasympathetic Cardiac Nerve Stimulation: An Approach for Stable Sinus Rate Control", *Journal of Cardiovascular Electrophysiology*, 10(11), (1999), 1517-1524.

Schauerte, P. N., "Transvenous Parasympathetic Nerve Stimulation in the Inferior Vena Cava and Atrioventricular Conduction", *Journal of Cardiovascular Electrophysiology*, 11(1), (2000), 64-69.

Sigurdsson, A., et al., "The Role of Neurohormonal Activation in Chronic Heart Failure and Postmyocardial Infarction", *American Heart Journal*, 132 (1 Pt 2 Su), (1996), 229-234.

Thompson, G. W., "Bradycardia Induced by Intravascular Versus Direct Stimulation of the Vagus Nerve", *Annals of Thoracic Surgery*, 65(3), (1998), 637-642.

Tyler, D. J., et al., "Chronic Response of the Rat Sciatic Nerve to the Flat Interface Nerve Electrode", *Annals of Biomedical Engineering*, 31(6), (2003), 633-642.

Vanoli, E., "Vagal Stimulation and Prevention of Sudden Death in Conscious Dogs with a Healed Myocardial Infarction", *Circulation Research*, 68(5), (1991), 1471-1481.

\* cited by examiner

SYSTEM FOR SELECTIVE ACTIVATION OF A NERVE TRUNK USING A TRANSVASCULAR RESHAPING LEAD

TECHNICAL FIELD

This disclosure relates generally to implantable medical devices and, more particularly, to systems for selective activation of a nerve trunk using a transvascular reshaping lead.

BACKGROUND

The autonomic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal function and works with the somatic nervous system. Autonomic balance reflects the relationship between parasympathetic and sympathetic activity. A change in autonomic balance is reflected in changes in heart rate, heart rhythm, cardiac contractility, remodeling, inflammation and blood pressure. Changes in autonomic balance can also be seen in other physiological changes, such as changes in abdominal pain, appetite, stamina, emotions, personality, muscle tone, sleep, and allergies, for example.

Reduced autonomic balance (increase in sympathetic and decrease in parasympathetic cardiac tone) during heart failure has been shown to be associated with left ventricular dysfunction and increased mortality. Research also indicates that increasing parasympathetic tone and reducing sympathetic tone may protect the myocardium from further remodeling and predisposition to fatal arrhythmias following myocardial infarction. Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult.

Selective activation has been defined as the ability to activate or stimulate single axons or small groups of axons (nerve bundles) within a common nerve trunk without stimulating other portions of the nerve. Selective activation is achievable through complex practices such as current steering, use of inter-neural electrodes, and use of selective geometries.

SUMMARY

The above-mentioned problems and others not expressly discussed herein are addressed by the present subject matter and will be understood by reading and studying this specification.

Disclosed herein, among other things, is a method for spreading nerve bundles in a nerve trunk. The method includes expanding an expandable portion of a lead, adapted to be chronically implanted in a blood vessel proximate a nerve trunk, to reshape the blood vessel to an elongated shape and to reshape the nerve trunk into an elongated shape to spread nerve bundles of the nerve trunk. The method also includes delivering an electrical signal from an implanted medical device to an electrode positioned at the expandable portion of the lead to transvascularly deliver neural stimulation from the electrode to at least one of the nerve bundles of the nerve trunk. According to various embodiments, delivering an electrical signal includes delivering neural stimulation to selectively activate the nerve trunk. According to various embodiments, expanding an expandable portion of a lead to reshape the nerve trunk to an elongated shape includes bringing neural fibers of interest closer to the one of the plurality of electrodes, reducing a threshold bias for stimulating the nerve trunk. According to further embodiments, expanding an expandable portion of a lead to reshape the nerve trunk to an elongated shape includes increasing available area for electrical contact placement.

One aspect of this disclosure relates to an electronic lead for spreading nerve bundles in a nerve trunk. According to one embodiment, the electronic lead includes a proximal portion adapted to connect to an implantable medical device and an expandable portion adapted to be chronically implanted in a blood vessel proximate a nerve trunk, the expandable portion further adapted to be expanded to reshape the blood vessel to an elongated shape and to reshape the nerve trunk into an elongated shape to spread nerve bundles of the nerve trunk. The electronic lead further includes a plurality of electrodes along the expandable portion of the lead, where an electrical signal is delivered from the implanted medical device to one of the plurality of electrodes to transvascularly deliver neural stimulation from the electrode to at least one of the nerve bundles of the nerve trunk.

One aspect of this disclosure relates to a system for spreading nerve bundles in a nerve trunk. According to one embodiment, the system includes a lead having a proximal portion and an expandable portion, the expandable portion adapted to be chronically implanted in a blood vessel proximate a nerve trunk, and the expandable portion further adapted to be expanded to reshape the blood vessel to an elongated shape and to reshape the nerve trunk into an elongated shape to spread nerve bundles of the nerve trunk. The system also includes a plurality of electrodes along the expandable portion of the lead and an implantable device coupled to the proximal portion of the lead. According to one embodiment, the implantable device includes a controller circuit to communicate with a neural stimulator, a telemetry circuit to communicate with the controller circuit and an external module, a memory circuit to communicate with the controller circuit, and computer-readable instructions embedded in the memory circuit. According to one embodiment, the computer-readable instructions are operable on by the controller to deliver an electrical signal to one of the plurality of electrodes to transvascularly deliver neural stimulation from the electrode to at least one of the nerve bundles of the nerve trunk.

Another aspect of this disclosure relates to a system for selective activation of a nerve trunk. According to one embodiment, the system includes means for generating a neural stimulation signal. The system also includes means for providing the neural stimulation signal to a nerve bundle, including means for chronically implanting a lead within a blood vessel proximate a nerve trunk, wherein the lead is adapted to expand and reshape the blood vessel and nerve trunk to spread the nerve bundles of the nerve trunk. According to various embodiments, the means for providing the neural stimulation includes a means for delivering neural stimulation to selectively activate the nerve trunk.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. The various embodiments are not necessarily mutually exclusive, as aspects of one embodiment can be combined with aspects of another embodiment. These embodiments are described in sufficient detail to enable those skilled in the art to practice the invention. Other embodiments may be utilized and structural, logical, and electrical changes may be made without departing from the scope of the present invention.

Neural stimulation has been the subject of a number of studies and has been proposed for several therapies. The autonomic system controls physiological activities of the body and the imbalance of autonomic tone is related to many diseases and conditions. Vagus nerve stimulation has been proposed to treat sleep disorders, gastrointestinal motility, eating disorders, obesity, anorexia, gastrointestinal tract disorders, hypertension, coma, and epilepsy. Direct electrical stimulation of parasympathetic nerves can induce a reduction of sympathetic nerve activity and reduce blood pressure by decreasing vascular resistance. Sympathetic inhibition, as well as parasympathetic activation, have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

Transvascular stimulation of a vagus nerve trunk is used in a number of therapies. In an example, vagal nerve stimulation simultaneously increases parasympathetic tone and decreases sympathetic myocardial tone. In an example, a vagus nerve trunk is transvascularly stimulated following cardiac ischemic insult. Increased sympathetic nervous activity following ischemia often results in increased exposure of the myocardium to epinephrine and norepinephrine. These catecholamines activate intracellular pathways within the myocytes, which lead to myocardial death and fibrosis. This effect is inhibited by stimulation of the parasympathetic nerves, such as vagus nerves. In an example, transvascular vagal stimulation from within the SVC lowers heart rate, overall blood pressure, and left ventricular pressure. Stimulation of the vagal cardiac nerves following myocardial infarction, or in heart failure patients, can be beneficial in preventing further remodeling and arrhythmogenesis.

In other examples, transvascular neural stimulation is used to treat other conditions such as hypertrophic cardiomyopathy (HCM) or neurogenic hypertension, where an increase parasympathetic cardiac tone and reduction in sympathetic cardiac tone is desired. In another example, a bradycardia condition is treated by transvascularly stimulating a sympathetic nerve trunk. In another example, the ionotropic state of the heart is increased by transvascularly stimulating a sympathetic nerve trunk. Transvascular sympathetic stimulation can also be used to treat orthostatic hypotension.

Selective activation (or selective stimulation) of nerve bundles within a nerve trunk has several benefits, including: allowing the ability to control one of a group of end organs; avoiding synergistic affects; decreasing the necessary stimulus amplitudes; and allowing coordinated movements or actions. Reshaping the nerve trunk improves access to nerve bundles for selective activation.

Transvascular Reshaping Lead

The lead apparatus disclosed herein is sometimes referred to as a transvascular reshaping lead, as the lead both delivers transvascular therapy and reshapes the surrounding vessel and adjacent nerve trunk. This provides for more reliable and efficient chronic selective activation, provides a greater amount of surface area for placement of stimulating electrodes, and allows for monophasic stimulation using lower amplitude and shorter pulse widths. In addition, the disclosed lead provides for a less invasive means for providing these benefits than using an intra-neural electrode or cuff electrode. As shown in the figures and discussed below, the disclosed lead reshapes the blood vessel by expanding asymmetrically along the radial axis of the vessel against the inner wall of the vessel, and reshapes the nerve trunk into an elongated shape as the vessel expands against the adjacent trunk. In this manner, the reshaping lead includes a transvascular prosthetic device.

The reshaping lead brings the nerve of interest into closer contact with the lead placed within the vessel, but it also serves as a stabilizing mechanism for the lead. By reshaping the vessel, the lead inherently also acts as its own fixation mechanism. In addition, the lead apparatus disclosed herein has the ability to sense an electrical signal from the nerve to be stimulated.

The lead can be used to stimulate or sense the nerve of interest when a vein, artery, or other vessel is running in close proximity to the nerve bundle. In one embodiment, the vessel and nerve bundle are within a common sheath.

Figure 1:
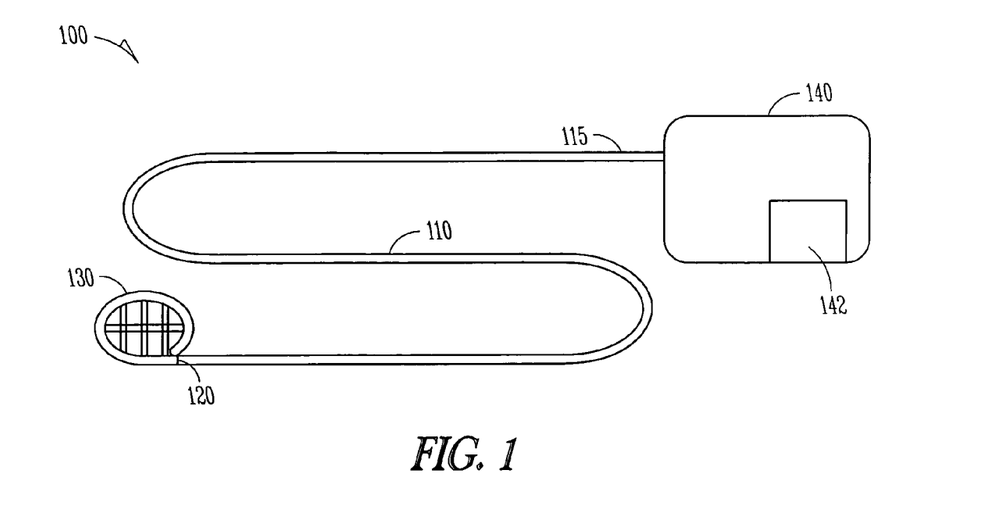
FIG. 1 illustrates a lead and an implantable medical device (IMD), according to one embodiment.

FIG. 1 illustrates a lead and an implantable medical device (IMD), according to one embodiment. Lead 100 includes a flexible lead body 110 extending from a proximal end 115 to a distal end 120. An expandable portion 130 is proximate the distal end 120 of lead body 110. As will be discussed below, expandable portion 130 is adapted to spread nerve bundles in a nerve trunk.

Lead 100 is coupled to an implantable medical device (IMD) 140, or pulse generator. Lead 100 includes conductors, such as coiled conductors that electrically couple pulse generator 140 to expandable portion 130. Accordingly, implantable medical device 140 can deliver a stimulation signal to via the proximal portion 130. The lead further includes outer insulation to insulate the conductor. The system can include a unipolar system with the case acting as an electrode or a bipolar system with a pulse between two distally located electrodes.

In one embodiment, implantable medical device 140 includes hardware, circuitry and software to perform neural stimulation functions, and includes controller circuitry 142. The controller circuitry 142 is capable of being implemented using hardware, software, and combinations of hardware and software. For example, according to various embodiments, the controller circuitry 142 includes a processor to perform instructions embedded in a memory to perform functions associated with neural stimulation, including selective activation. The lead is adapted to be placed intravenously in a blood vessel. In one embodiment, the lead is placed intravenously through the inferior jugular vein. In another embodiment, the lead is placed intravenously through the subclavian vein. The lead is adapted to be placed in other vessels, as will be discussed below with respect to FIGS. 8A-8E.

Figure 2:
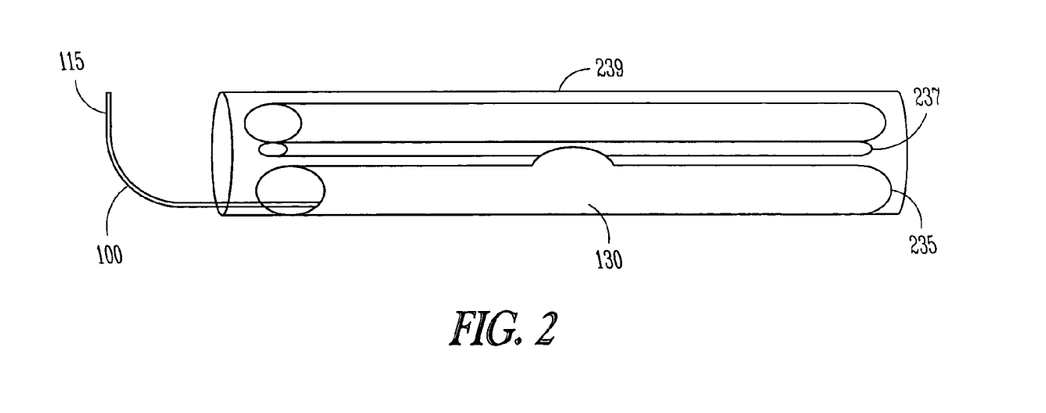
FIG. 2 illustrates an apparatus for spreading nerve bundles in a nerve trunk, according to one embodiment.

FIG. 2 illustrates an apparatus for spreading nerve bundles in a nerve trunk, according to one embodiment. An electronic lead 100 is shown for spreading nerve bundles in a nerve trunk. According to one embodiment, the electronic lead 100 includes a proximal portion 115 adapted to connect to an implantable medical device and an expandable portion 130 adapted to be chronically implanted in a blood vessel 235 proximate a nerve trunk 237, the expandable portion further adapted to be expanded to asymmetrically expand the blood vessel against the nerve trunk to reshape the nerve trunk and spread nerve bundles of the nerve trunk. In one embodiment, the vessel and nerve bundle are within a common sheath 239.

Figure 3A:
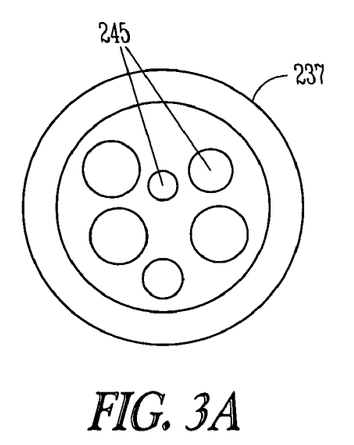
FIG. 3A illustrates an example of nerve bundles in a nerve trunk, according to one embodiment.

FIG. 3A illustrates an example of nerve bundles 245 in a nerve trunk 237, according to one embodiment. The depicted nerve trunk 237 is cylindrical and contains a plurality of cylindrical nerve bundles 245, or groups of axons. The overlapping of the bundles 245 creates an obstacle to selective transvascular activation of specific nerve bundles without affecting neighboring bundles.

Figure 3B:
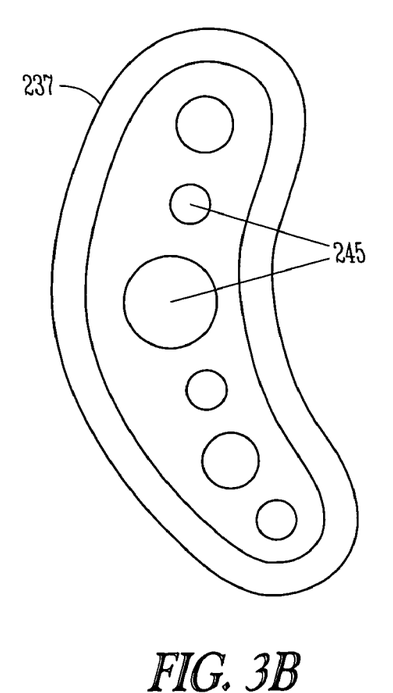
FIG. 3B illustrates spreading nerve bundles in a nerve trunk, according to one embodiment.

FIG. 3B illustrates spreading nerve bundles in a nerve trunk, according to one embodiment. The nerve trunk of FIG. 3B is shown after the present system has reshaped the nerve trunk into an elongated shape by asymmetrically expanding the adjacent blood vessel to "flatten out" or spread the trunk 237. The reshaped trunk 237 contains a spread of nerve bundles 245. The depicted embodiment shows the reorganized bundles 245 in a row. Those of skill in the art will appreciate that specific nerve bundles (or fascicles) can more easily be targeted for selective activation in this geometry, as neural fibers of interest are brought closer to the electrode containing lead. Selective activation can then be achieved using simple monophasic low current amplitude stimuli, or using field steering techniques. In addition, selective activation can be achieved chronically in this setting, and an increased area for electrical contact placement is provided.

An embodiment of the electronic lead, like the one shown at 100 in FIG 2, includes a biased, expandable portion. In this embodiment, a plurality of discrete electrodes is placed around the outer circumference of the expandable portion. According to various embodiments, an electrical signal is delivered from the implanted medical device to one of the plurality of electrodes to transvascularly deliver neural stimulation from the electrode to at least one of the nerve bundles of the nerve trunk. In other embodiments, the entire biased oval portion can be an exposed electrode. Oval biased expandable portion is dimensioned to expand the distal end to asymmetrically expand a blood vessel against the nerve trunk to reshape the nerve trunk and spread nerve bundles of the nerve trunk. Other embodiments can use other angles as needed. In an embodiment, the expandable portion includes an electroactive polymer, or shape memory polymer, that is pre-molded in a desired configuration and collapsible to be delivered through a catheter.

Besides an oval design, the electronic lead can have other configurations to reshape vessels and nerve trunks. In one embodiment, the lead is a stent design to reshape the vessel and has an area of high contact density to increase selective activation techniques. The stent can be deployed by a balloon that expands only in one radial direction to produce a flattened oval shape. In one embodiment, the stent can be made of nitinol to retain its shape once deployed and after any trauma that may occur to the vessel after deployment. In another embodiment, the lead is a bias lead that will also have capability to reshape the vessel and have many electrical contacts for stimulation. A mechanically expandable lead using a screw located at the proximal end is included in a further embodiment. In this embodiment, turning the screw expands a series of spines to asymmetrically expand the lead. An example of this embodiment includes three spines on opposite sides of the lead body including a middle spine and two shorter adjacent spines, and turning the screw shortens the lead and expands the middle spine outward and expands the two adjacent spines that straddle the middle spine outward to a lesser extent than the middle spine.

System for Delivering Selective Transvascular Stimulation

Figure 4:
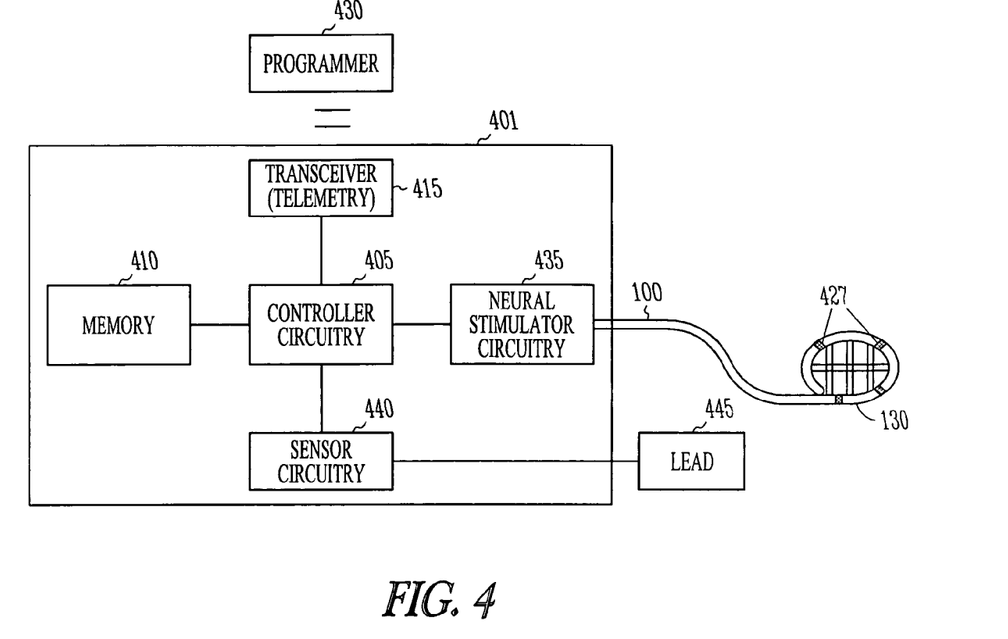
FIG. 4 is a schematic illustration of an implantable system for delivering selective transvascular stimulation, according to one embodiment.

FIG. 4 is a schematic illustration of an implantable system for delivering selective transvascular stimulation, according to one embodiment. The system includes an implantable device 401, an electrical lead 100 coupled to the implantable device 401, and an expandable portion 130 of the lead containing stimulation electrodes 427. The implantable device includes a controller circuit 405, a memory circuit 410, a telemetry circuit 415, and a neural stimulation circuit 435. The controller circuit 405 is operable on instructions stored in the memory circuit to deliver an electrical stimulation therapy. Therapy is delivered by the neural stimulation circuit 435 through the lead 100 and the electrodes 427. The telemetry circuit 415 allows communication with an external programmer 430. The illustrated system also includes optional sensor circuitry 440 that is coupled to a lead 445. In various embodiments, the electrical lead 100 having the expandable portion can function as a sensor lead. The controller circuit 405 processes sensor data from the sensor circuitry and delivers a therapy responsive to the sensor data.

Figure 5:
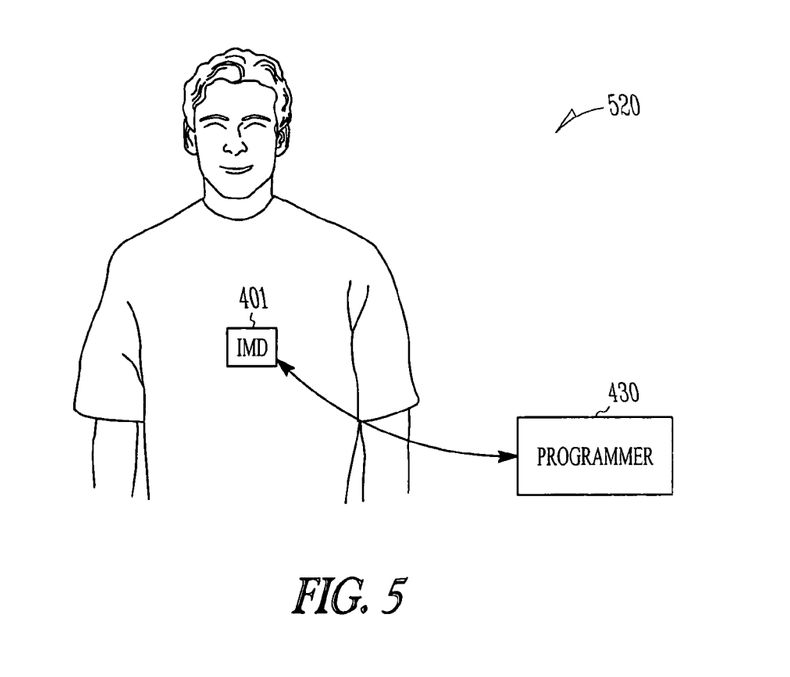
FIG. 5 illustrates a system including an implantable medical device (IMD) and a programmer, according to one embodiment.

FIG. 5 illustrates a system 520 including an implantable medical device (IMD) 401 and a programmer 430, according to one embodiment. Various embodiments of the IMD 401 include neural stimulator functions only, and various embodiments include a combination of neural stimulation and cardiac rhythm management functions. The programmer 430 and the IMD 401 are capable of wirelessly communicating data and instructions. In various embodiments, for example, the programmer 430 and IMD 401 use telemetry coils to wirelessly communicate data and instructions. Thus, the programmer can be used to adjust the programmed therapy provided by the IMD 401 and the IMD can report device data (such as battery and lead resistance) and therapy data (such as sense and stimulation data) to the programmer using radio telemetry, for example. According to various embodiments, the IMD 401 selectively stimulates nerve bundles spread using the method disclosed in FIG. 7 below. According to various embodiments, the IMD 401 includes a sensor to sense ANS activity. Such a sensor can be used to perform feedback in a closed loop control system. For example, various embodiments sense surrogate parameters, such as respiration and blood pressure, indicative of ANS activity. According to various embodiments, the IMD further includes cardiac stimulation capabilities, such as pacing and defibrillating capabilities in addition to the capabilities to stimulate nerve bundles and/or sense ANS activity.

Figure 6:
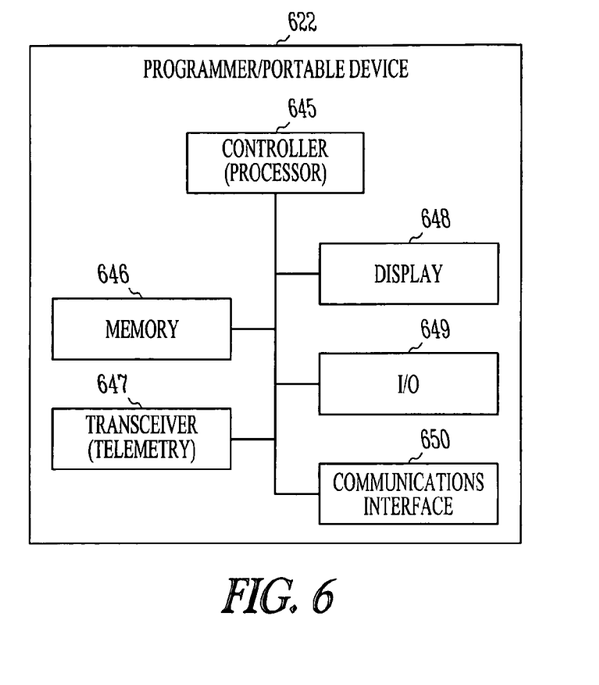
FIG. 6 illustrates a programmer such as illustrated in the system of FIG. 5 or other external device to communicate with the implantable medical device(s), according to one embodiment.

FIG. 6 illustrates a portable device 622, such as the programmer 430 illustrated in the system of FIG. 5 or other external device to communicate with the implantable medical device(s), according to one embodiment. An example of another external device includes Personal Digital Assistants (PDAs) or personal laptop and desktop computers in an Advanced Patient Management (APM) system. The illustrated device 622 includes controller circuitry 645 and a memory 646. The controller circuitry 645 is capable of being implemented using hardware, software, and combinations of hardware and software. For example, according to various embodiments, the controller circuitry 645 includes a processor to perform instructions embedded in the memory 646 to perform a number of functions, including communicating data and/or programming instructions to the implantable devices. The illustrated device 622 further includes a transceiver 647 and associated circuitry for use to communicate with an implantable device. Various embodiments have wireless communication capabilities. For example, various embodiments of the transceiver 647 and associated circuitry include a telemetry coil for use to wirelessly communicate with an implantable device. The illustrated device 622 further includes a display 648, input/output (I/O) devices 649 such as a keyboard or mouse/pointer, and a communications interface 650 for use to communicate with other devices, such as over a communication network.

Method for Spreading Nerve Bundles

Figure 7:
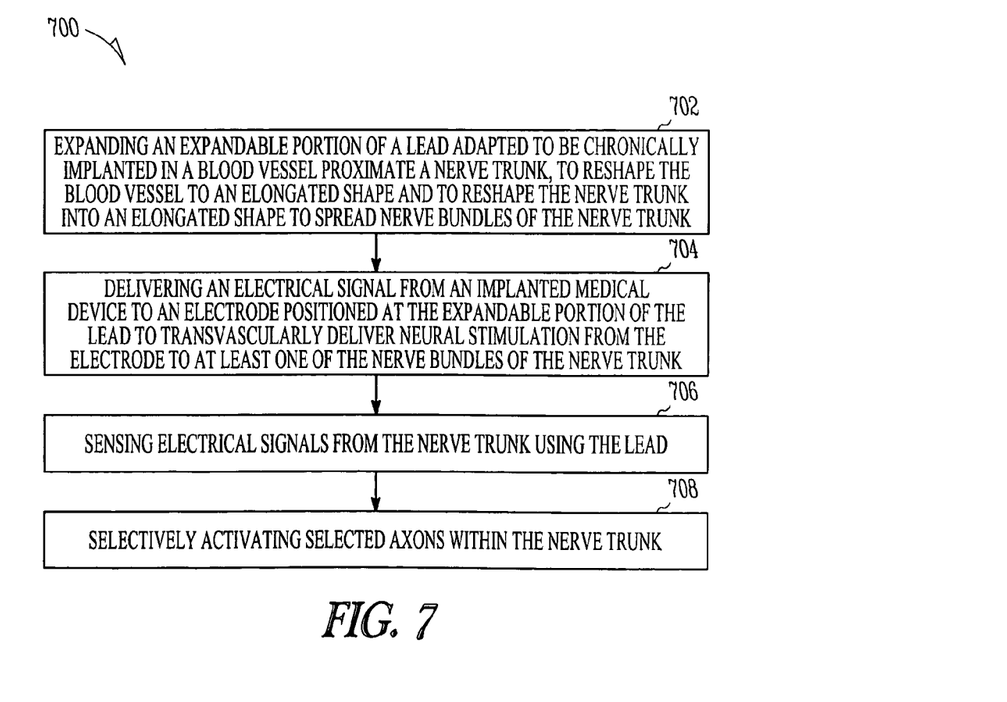
FIG. 7 illustrates a flow diagram of a method for spreading nerve bundles in a nerve trunk, according to one embodiment.

FIG. 7 illustrates a flow diagram of a method for spreading nerve bundles in a nerve trunk, according to one embodiment. The method 700 includes expanding an expandable portion of a lead, adapted to be chronically implanted in a blood vessel proximate a nerve trunk, to reshape the blood vessel to an elongated shape and to reshape the nerve trunk into an elongated shape to spread nerve bundles of the nerve trunk, at 702. The method also includes delivering an electrical signal from an implanted medical device to an electrode positioned at the expandable portion of the lead to transvascularly deliver neural stimulation from the electrode to at least one of the nerve bundles of the nerve trunk, at 704. In one embodiment, the vessel and nerve bundle are within a common sheath.

According to an embodiment, the method includes sensing electrical signals from the nerve targeted for stimulation, at 706. According to various embodiments, delivering an electrical signal includes delivering neural stimulation to selectively activate small amounts of axons within the nerve trunk, at 708. Not all embodiments of the disclosed method use all steps depicted in FIG. 7.

According to various embodiments, expanding an expandable portion of a lead to reshape the nerve trunk to an elongated shape includes bringing neural fibers of interest closer to the one of the plurality of electrodes, reducing a threshold bias for stimulating the nerve trunk. According to further embodiments, expanding an expandable portion of a lead to reshape the nerve trunk to an elongated shape includes increasing available area for electrical contact placement. The disclosed method takes advantage of cervical anatomy to reshape the geometry of a nerve to position neural tissue where simple stimulation protocols can be used to selectively activate small sub-populations of fibers, according to various embodiments. In addition, in an embodiment the lead selectively activates afferent or efferent axons within the nerve bundle.

Lead Placement Targets

Figure 8A:
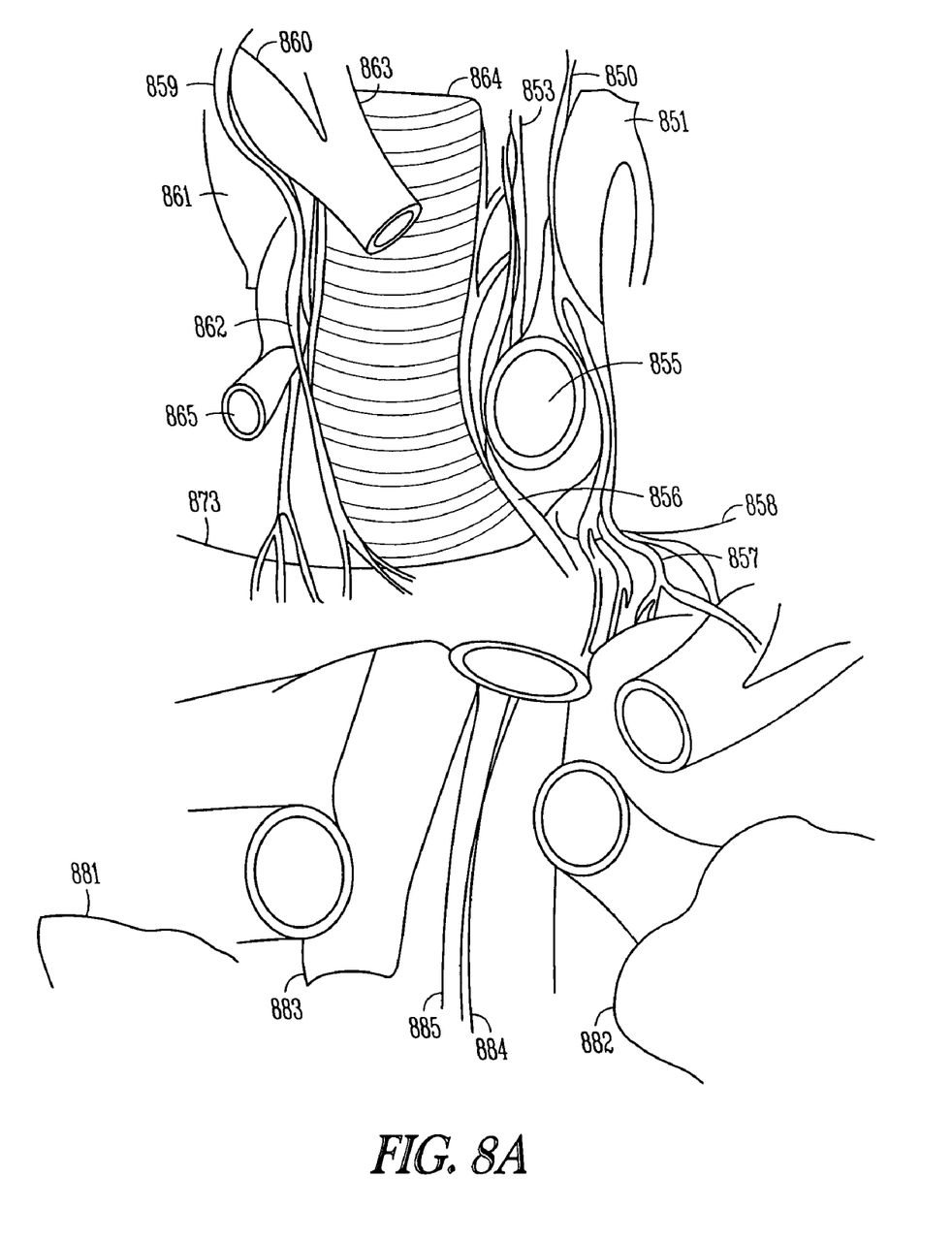
FIGS. 8A and 8B are illustrations of blood vessels and nerve trunks used by the present system, according to various embodiments.
Figure 8B:
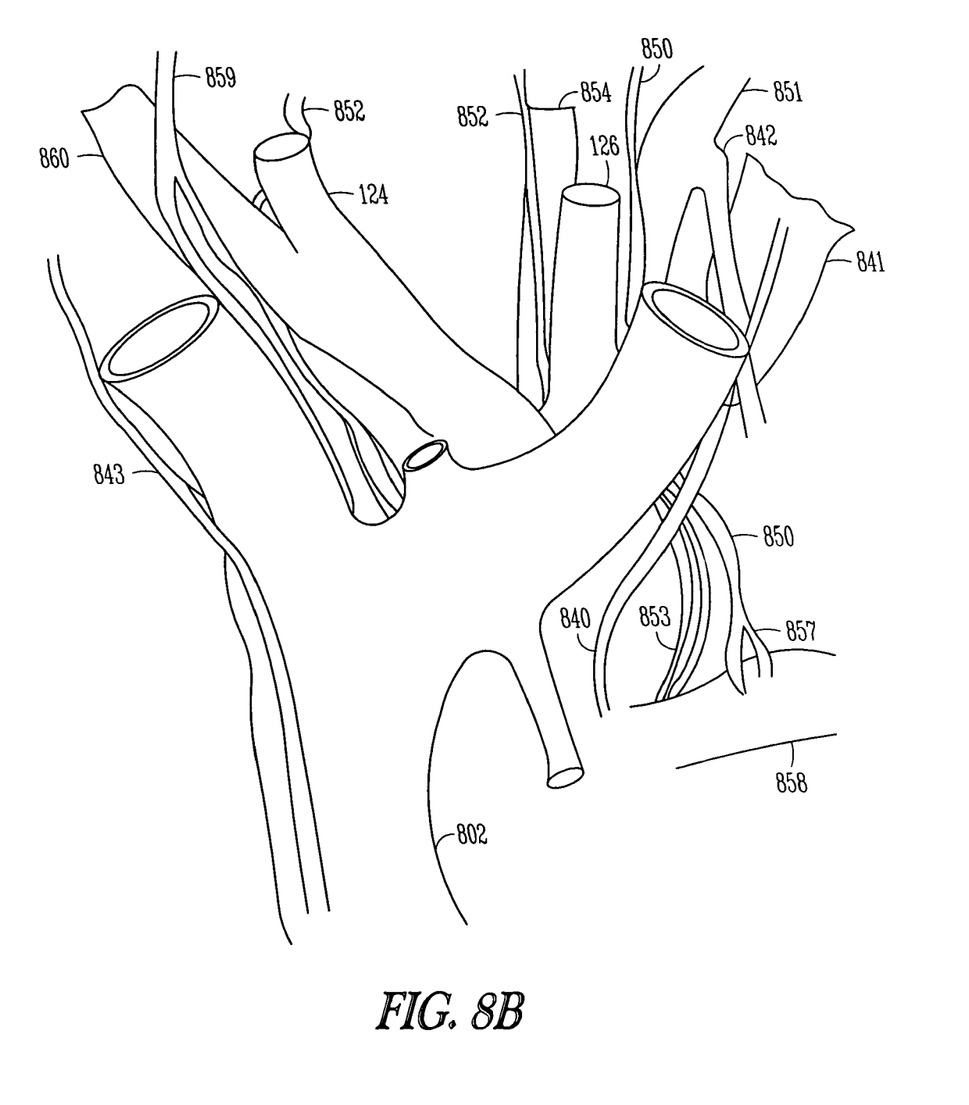

FIGS. 8A and 8B are illustrations of blood vessels and nerve trunks used by the present system, according to various embodiments. FIG. 8A shows left vagus nerve 850 extending next to a subdlavian artery 851. Various nerves extend around the arch of the aorta 855. Vagus nerve 850 also extends past the ligamentum arteriosum 856. The anterior pulmonary plexus 857 crosses the left pulmonary artery 858. Right vagus nerve 859 extends past a subdlavian artery 860 and the cupola of pleura 861. Cardiac nerves 862 extend past the brachiocephalic trunk 863 near the trachea 864. Cardiac nerves 862 also extend past the arch of an azygos vein 865 to the right pulmonary artery 873. In the lower portion of FIG. 8A appear the right lung 881, left lung 882, esophagus 883, a lower portion 884 of the left vagus nerve 850, and a lower portion 885 of the aorta. FIG. 8B shows a left phrenic nerve 840 extending past a cupola of pleura 841, an internal thoracic artery 842, and left pulmonary artery 858 Vagus nerve 850, recurrent laryngeal nerves 852, cardiac nerves 853, and the anterior pulmonary plexus 857 extend near the left pulmonary artery 858 and ligamentum arteriosum. A lead with an expandable portion containing electrodes, such as a stent, is chronically implantable in the blood vessels shown in FIGS. 8A or 8B to selectively transvascularly stimulate a nerve or nerve trunk that extends on or near the blood vessel. In one example, the vagus nerve is transvascularly stimulated from the azygos vein 865 or internal jugular vein.

Figure 8C:
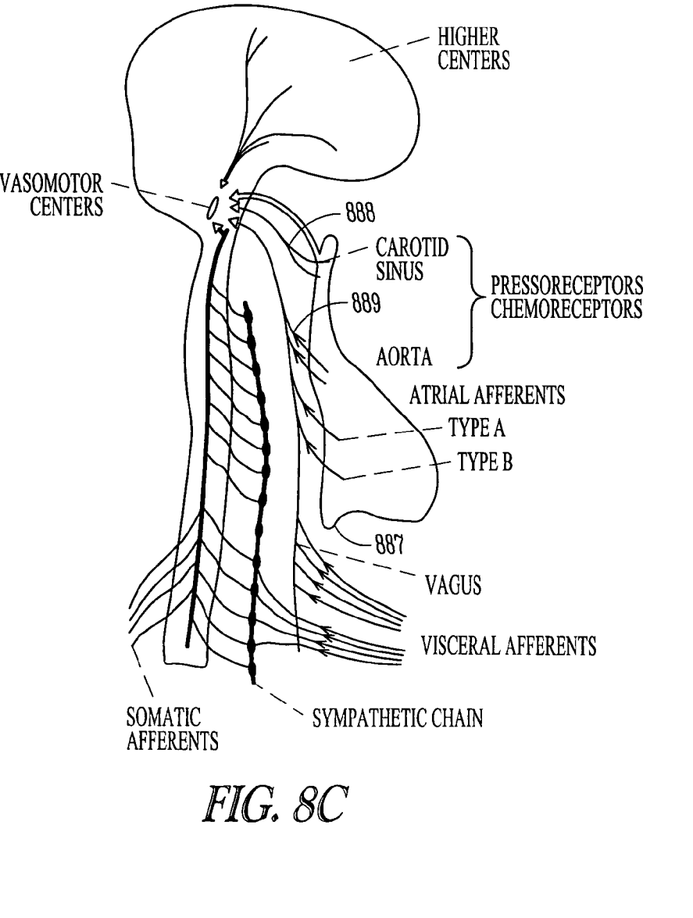
FIGS. 8C and 8D show neural pathways targeted by the present system, according to various embodiments.
Figure 8D:
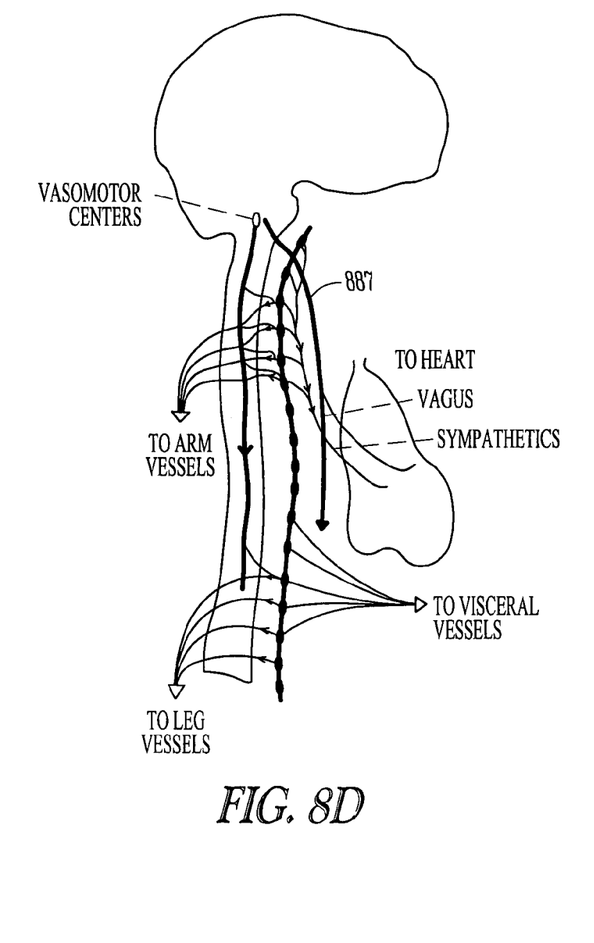

FIGS. 8C and 8D show neural pathways targeted by the present system, according to various embodiments. FIG. 8C generally illustrates afferent nerves to vasomotor centers. An afferent nerve conveys impulses toward a nerve center. A vasomotor center relates to nerves that dilate and constrict blood vessels to control the size of the blood vessels. FIG. 8D generally illustrates efferent nerves from vasomotor centers. An efferent nerve conveys impulses away from a nerve center. Afferent and efferent nerves can be stimulated transvascularly.

Figure 8E:
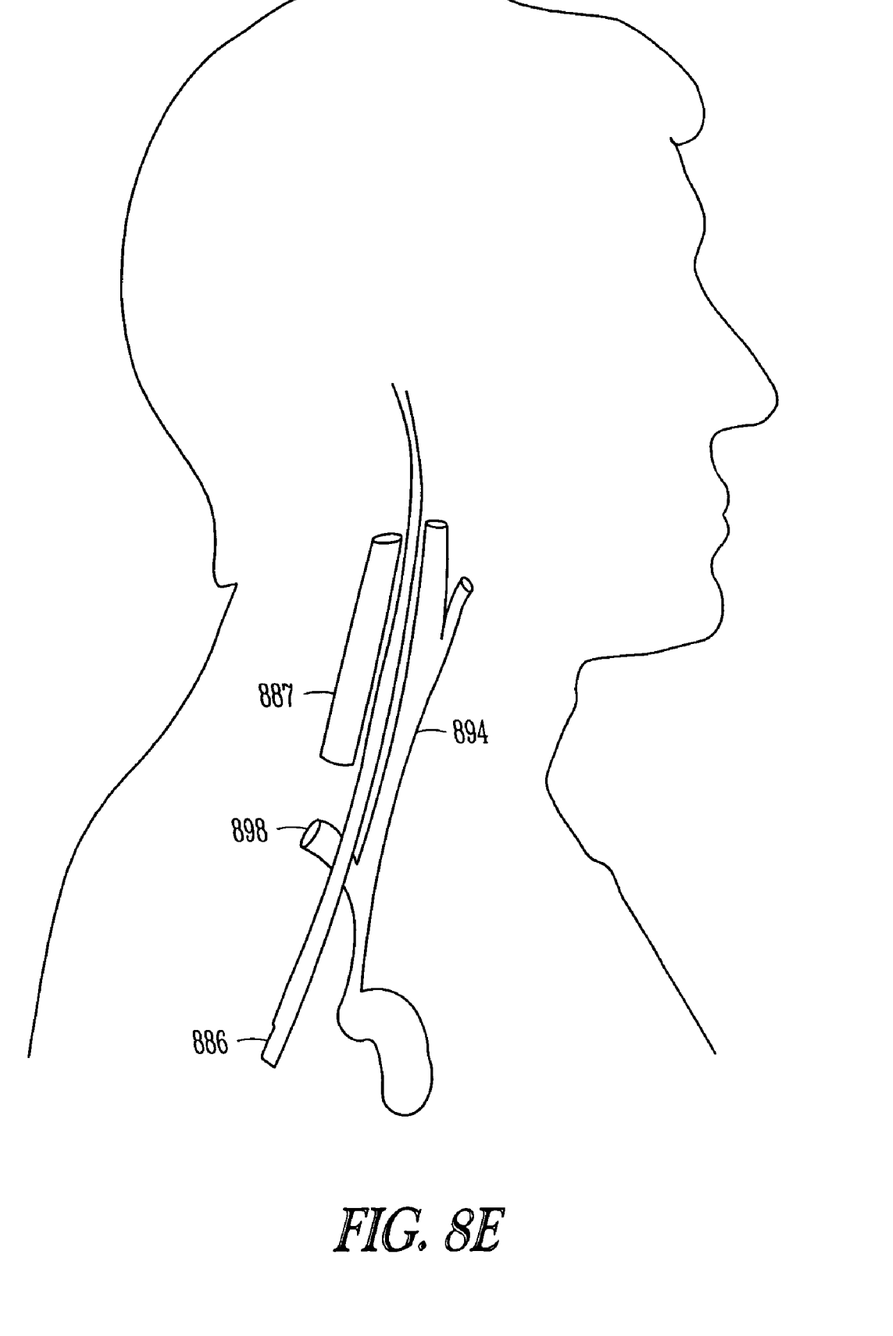
FIG. 8E is an illustration of an internal jugular vein near a vagus nerve for chronic implantation of the present apparatus, according to various embodiments.

FIG. 8E is an illustration of an internal jugular vein 887 near a vagus nerve 886 for chronic implantation of the present apparatus, according to various embodiments. In an example, the vagus nerve 886 is transvascularly stimulated from the internal jugular vein 887. A common carotid artery 894 and subclavian artery 898 are also shown in FIG. 8E. In other examples, nerve trunks innervating other organs, such as the lungs or kidneys are transvascularly stimulated. In an example, an expandable electrode such as a stent is implanted in a blood vessel proximate a nerve or nerve trunk that innervates the lungs or kidneys.

The vagus nerve includes a left and right vagus nerve. The right vagus nerve passes anterior to the subclavian artery, breaks up into pulmonary plexus posterior to root of the right lung, refers and then breaks up into esophageal and cardiac plexuses. The left vagus nerve passes to the left of the aortic arch and posterior to the root of the left lung, giving pulmonary, esophageal and cardiac plexuses. The described lead(s)

provide minimally-invasive means to provide vagal stimulation, including selective vagal activation. Vagal nerve stimulation (VNS) can be used with the following control measures: R-R interval; P-R interval; Q-T interval; systolic pressure; diastolic pressure; MAP; stroke volume; respiratory rate; tidal volume; temperature; activity level; EEG; EMG; wake/sleep state; apnea/hypopnea Index; ENG; and EOG. Those of skill in the art will recognize that other control measures can be associated with VNS using the disclosed system.

While the above description discusses utilization of the present system adjacent the vagal nerve, the system can be used anywhere in a human body where a major vessel is running next to a nerve. Examples include but are not limited to the femoral nerve and the ulna/median nerve. In one embodiment, the vessel and nerve bundle are within a common sheath. In addition, the system can be used to sense and measure vessel characteristics.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An electrical lead, comprising:
   a proximal portion adapted to connect to an implantable medical device;
   an expandable portion adapted to be chronically implanted in a blood vessel proximate a nerve trunk, the expandable portion further adapted to be expanded to asymmetrically expand the blood vessel against the nerve trunk to reshape the nerve trunk and spread nerve bundles of the nerve trunk; and
   a plurality of electrodes along the expandable portion of the lead;
   wherein an electrical signal is delivered from the implanted medical device to one of the plurality of electrodes to transvascularly deliver neural stimulation from the electrode to at least one of the nerve bundles of the nerve trunk.

2. The electrical lead of claim 1, wherein the expandable portion includes an oval shape.

3. The electrical lead of claim 1, wherein the expandable portion includes a stent.

4. The electrical lead of claim 1, wherein the expandable portion includes a bias lead.

5. The electrical lead of claim 1, wherein the expandable portion is configured to be implanted in a blood vessel proximate a peripheral nerve trunk.

6. The electrical lead of claim 5, wherein the expandable portion is configured to be implanted in a blood vessel proximate a sympathetic nerve.

7. The electrical lead of claim 5 wherein the expandable portion is configured to be implanted in a blood vessel proximate a parasympathetic nerve.

8. The electrical lead of claim 5, wherein the expandable portion is configured to be implanted in a blood vessel proximate a vagal cardiac nerve.

9. The electrical lead of claim 8, wherein the expandable portion is configured to be implanted in the internal jugular vein within a carotid sheath.

10. The electrical lead of claim 5, wherein the expandable portion is adapted to be implanted in a blood vessel proximate a femoral nerve trunk.

11. The electrical lead of claim 5, wherein the expandable portion is adapted to be implanted in a blood vessel proximate an ulna nerve trunk.

12. A system, comprising:
   a lead having a proximal portion and an expandable portion, the expandable portion adapted to be chronically implanted in a blood vessel proximate a nerve trunk, and the expandable portion further adapted to be expanded to reshape the blood vessel to an elongated shape and to reshape the nerve trunk into an elongated shape to spread nerve bundles of the nerve trunk;
   a plurality of electrodes along the expandable portion of the lead; and
   an implantable device coupled to the proximal portion of the lead, the implantable device including:
      a neural stimulator; and
      a controller to communicate with the neural stimulator, the controller being adapted to deliver an electrical signal to one of the plurality of electrodes to transvascularly deliver neural stimulation from the electrode to at least one of the nerve bundles of the nerve trunk.

13. The system of claim 12, wherein the lead includes an oval shaped lead.

14. The system of claim 12, wherein the lead includes a stent.

15. The system of claim 12, wherein the lead includes a bias lead.

16. The system of claim 12, wherein the lead is configured for implantation proximate a vagal cardiac nerve.

17. The system of claim 16, wherein the lead is implantable in a blood vessel proximate a vagal cardiac nerve and the instructions are operable on by the controller to deliver a programmable electric pulse therapy to transvascularly stimulate the vagal cardiac nerve to inhibit cardiac remodeling.

18. A system, comprising:
means for generating a neural stimulation signal; and
means for providing the neural stimulation signal to a nerve bundle, including means for chronically implanting a lead within a blood vessel proximate a nerve trunk, wherein the lead is adapted to be expanded to asymmetrically expand the blood vessel against the nerve trunk to reshape the nerve trunk and spread nerve bundles of the nerve trunk.

19. The system of claim 18, wherein the means for providing the neural stimulation includes a means for delivering neural stimulation to selectively activate the nerve trunk.

20. The system of claim 18, wherein the means for providing the neural stimulation includes a plurality of electrodes along the lead.

21. The system of claim 20, wherein the lead is adapted to reshape the nerve trunk to bring neural fibers of interest closer to the one of the plurality of electrodes, reducing a threshold bias for stimulating the nerve trunk.

22. The system of claim 18, wherein the lead is adapted to reshape the nerve trunk to increase available area for electrical contact placement.

23. The system of claim 18, wherein the lead is configured for implantation proximate a vagal cardiac nerve.

24. A method, comprising:
reshaping a blood vessel proximate a nerve trunk to an elongated shape thereby reshaping the nerve trunk into an elongated shape to spread nerve bundles of the nerve trunk, wherein reshaping the blood vessel includes expanding an expandable portion of a lead adapted to be chronically implanted in the blood vessel; and
delivering an electrical signal from an implanted medical device to an electrode positioned at the expandable portion of the lead to transvascularly deliver neural stimulation from the electrode to at least one of the nerve bundles of the nerve trunk.

25. The method of claim 24, wherein delivering an electrical signal includes delivering neural stimulation to selectively activate small amounts of axons within the nerve trunk.

26. The method of claim 24, wherein delivering an electrical signal includes delivering neural stimulation to selectively activate afferent axons within the nerve bundle.

27. The method of claim 24, wherein delivering an electrical signal includes delivering neural stimulation to selectively activate efferent axons within the nerve bundle.

28. The method of claim 24, wherein expanding an expandable portion of a lead to reshape the nerve trunk to an elongated shape includes bringing neural fibers of interest closer to the one of the plurality of electrodes, reducing a threshold bias for stimulating the nerve trunk.

29. The method of claim 24, wherein expanding an expandable portion of a lead to reshape the nerve trunk to an elongated shape includes increasing available area for electrical contact placement.

30. The method of claim 24, wherein expanding an expandable portion of a lead, adapted to be chronically implanted in a blood vessel proximate a nerve trunk includes expanding an expandable portion of a lead, adapted to be chronically implanted in a internal jugular vein proximate a vagal nerve trunk within a carotid sheath.

31. The method of claim 30, wherein delivering an electrical signal includes delivering neural stimulation to selectively activate the vagal nerve trunk.

32. The method of claim 30, wherein expanding an expandable portion of a lead to reshape the vagal nerve trunk to an elongated shape includes bringing vagal neural fibers of interest closer to the one of the plurality of electrodes, reducing a threshold bias for stimulating the vagal nerve trunk.

33. The method of claim 30, wherein expanding an expandable portion of a lead to reshape the vagal nerve trunk to an elongated shape includes increasing available area for electrical contact placement.

34. The method of claim 24, wherein expanding an expandable portion of a lead to reshape the blood vessel includes asymmetrically expanding the expandable portion of the lead.

35. The method of claim 24, further comprising:
sensing electrical signals from the nerve trunk using the lead.

36. A method, comprising:
expanding an expandable portion of a lead, adapted to be chronically implanted in a blood vessel proximate a nerve trunk, to reshape the blood vessel to an elongated shape and to reshape the nerve trunk into an elongated shape to spread nerve bundles of the nerve trunk; and
delivering an electrical signal from an implanted medical device to an electrode positioned at the expandable portion of the lead to transvascularly deliver neural stimulation from the electrode to at least one of the nerve bundles of the nerve trunk,
wherein delivering an electrical signal includes delivering neural stimulation to selectively activate small amounts of axons within the nerve trunk.

37. A method, comprising:
expanding an expandable portion of a lead, adapted to be chronically implanted in a blood vessel proximate a nerve trunk, to reshape the blood vessel to an elongated shape and to reshape the nerve trunk into an elongated shape to spread nerve bundles of the nerve trunk; and
delivering an electrical signal from an implanted medical device to an electrode positioned at the expandable portion of the lead to transvascularly deliver neural stimulation from the electrode to at least one of the nerve bundles of the nerve trunk,
wherein delivering an electrical signal includes delivering neural stimulation to selectively activate afferent axons within the nerve bundle.

38. A method, comprising:
expanding an expandable portion of a lead, adapted to be chronically implanted in a blood vessel proximate a nerve trunk, to reshape the blood vessel to an elongated shape and to reshape the nerve trunk into an elongated shape to spread nerve bundles of the nerve trunk; and
delivering an electrical signal from an implanted medical device to an electrode positioned at the expandable portion of the lead to transvascularly deliver neural stimulation from the electrode to at least one of the nerve bundles of the nerve trunk,
wherein delivering an electrical signal includes delivering neural stimulation to selectively activate efferent axons within the nerve bundle.

39. A method, comprising:
expanding an expandable portion of a lead, adapted to be chronically implanted in a blood vessel proximate a nerve trunk, to reshape the blood vessel to an elongated shape and to reshape the nerve trunk into an elongated shape to spread nerve bundles of the nerve trunk; and
delivering an electrical signal from an implanted medical device to an electrode positioned at the expandable portion of the lead to transvascularly deliver neural stimulation from the electrode to at least one of the nerve bundles of the nerve trunk,
wherein expanding an expandable portion of a lead, adapted to be chronically implanted in a blood vessel proximate a nerve trunk includes expanding an expandable portion of a lead, adapted to be chronically implanted in a internal jugular vein proximate a vagal nerve trunk within a carotid sheath.

40. The method of claim 39, wherein delivering an electrical signal includes delivering neural stimulation to selectively activate the vagal nerve trunk.

41. The method of claim 39, wherein expanding an expandable portion of a lead to reshape the vagal nerve trunk to an elongated shape includes bringing vagal neural fibers of interest closer to the one of the plurality of electrodes, reducing a threshold bias for stimulating the vagal nerve trunk.

42. The method of claim 39, wherein expanding an expandable portion of a lead to reshape the vagal nerve trunk to an elongated shape includes increasing available area for electrical contact placement.

* * * * *

UNITED STATES PATENT AND TRADEMARK OFFICE
CERTIFICATE OF CORRECTION

PATENT NO. : 7,617,003 B2  Page 1 of 1
APPLICATION NO. : 11/130022
DATED : November 10, 2009
INVENTOR(S) : Caparso et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1207 days.

Signed and Sealed this

Nineteenth Day of October, 2010

David J. Kappos
*Director of the United States Patent and Trademark Office*